(12) United States Patent
Goldstein

(10) Patent No.: US 7,860,659 B2
(45) Date of Patent: *Dec. 28, 2010

(54) METHODS AND SYSTEMS FOR PROVIDING A NUTRACEUTICAL PROGRAM SPECIFIC TO AN INDIVIDUAL ANIMAL

(75) Inventor: Robert S. Goldstein, Bridgeport, CT (US)

(73) Assignee: Bionutritional, LLC, South Salem, NY (US)

(*) Notice: Subject to any disclaimer, the term of this patent is extended or adjusted under 35 U.S.C. 154(b) by 67 days.

This patent is subject to a terminal disclaimer.

(21) Appl. No.: 12/313,572

(22) Filed: Nov. 21, 2008

(65) Prior Publication Data

US 2009/0130702 A1  May 21, 2009

Related U.S. Application Data

(60) Continuation-in-part of application No. 12/157,106, filed on Jun. 6, 2008, which is a division of application No. 11/228,571, filed on Sep. 15, 2005, now Pat. No. 7,409,297.

(60) Provisional application No. 60/610,748, filed on Sep. 17, 2004.

(51) Int. Cl.
   *G06F 7/00* (2006.01)
(52) U.S. Cl. .................. 702/19; 702/20; 436/501; 435/7.1
(58) Field of Classification Search .................. None
    See application file for complete search history.

(56) References Cited

U.S. PATENT DOCUMENTS

| | | | |
|---|---|---|---|
| 4,362,710 A | 12/1982 | Watanabe | |
| 4,863,873 A | 9/1989 | Matson | |
| 5,296,243 A | 3/1994 | Lange et al. | |
| 5,355,833 A | 10/1994 | Legrain | |
| 5,536,509 A * | 7/1996 | Protti | 426/2 |
| 5,551,374 A | 9/1996 | Wells | |
| 5,579,719 A | 12/1996 | Hoff et al. | |
| RE35,699 E | 12/1997 | Lange et al. | |
| 5,836,312 A | 11/1998 | Moore | |
| 5,840,020 A | 11/1998 | Heinonen et al. | |
| 5,954,640 A * | 9/1999 | Szabo | 600/300 |
| 5,955,122 A | 9/1999 | Petersen | |
| 6,000,361 A | 12/1999 | Pratt | |
| 6,032,084 A | 2/2000 | Anderson et al. | |
| 6,047,259 A | 4/2000 | Campbell et al. | |
| 6,287,254 B1 | 9/2001 | Dodds | |
| 6,537,213 B2 | 3/2003 | Dodds | |
| 6,562,378 B1 | 5/2003 | Chandra | |
| 6,730,023 B1 | 5/2004 | Dodds | |
| 7,029,441 B2 | 4/2006 | Dodds | |
| 7,134,995 B2 | 11/2006 | Dodds | |
| 7,409,297 B2 * | 8/2008 | Goldstein | 702/19 |
| 7,548,839 B2 | 6/2009 | Dodds | |
| 7,552,039 B2 | 6/2009 | Dodds | |
| 2002/0004749 A1 | 1/2002 | Froseth et al. | |
| 2002/0022772 A1 | 2/2002 | Dodds | |
| 2002/0059158 A1 | 5/2002 | Goldman et al. | |
| 2002/0187480 A1 * | 12/2002 | Brandon | 435/6 |
| 2004/0143403 A1 * | 7/2004 | Brandon et al. | 702/19 |
| 2005/0090718 A1 | 4/2005 | Dodds | |
| 2009/0132465 A1 | 5/2009 | Dodds | |
| 2009/0254327 A1 | 10/2009 | Dodds | |

OTHER PUBLICATIONS

Turnlund J.R., "Future Directions for Establishing Mineral/Trace Element Requirements," Journal of Nutrition, vol. 124, pp. 1765S-1770S, 1994.

* cited by examiner

*Primary Examiner*—Mary K Zeman
(74) *Attorney, Agent, or Firm*—Lipsitz & McAllister, LLC

(57) ABSTRACT

The present invention relates to methods and systems for providing an animal with a nutraceutical program that is specifically tailored to address the deficiencies and/or needs of the particular animal. Blood is drawn from the animal and analyzed at a lab to obtain blood test results. The blood test results are scored to obtain at least one blood test score for at least one corresponding blood parameter. If the at least one blood test score falls within a normal range but outside of an optimal range, one or more nutraceuticals needed to bring the animal within the optimal range for the at least one corresponding blood parameter are identified. A prescribed dosage amount is then calculated for at least one of the one or more identified nutraceuticals for the animal. The calculation of the prescribed dosage amount is based on at least the blood test score for the corresponding blood parameter and a deviation of the blood test score from the optimal range.

19 Claims, 3 Drawing Sheets

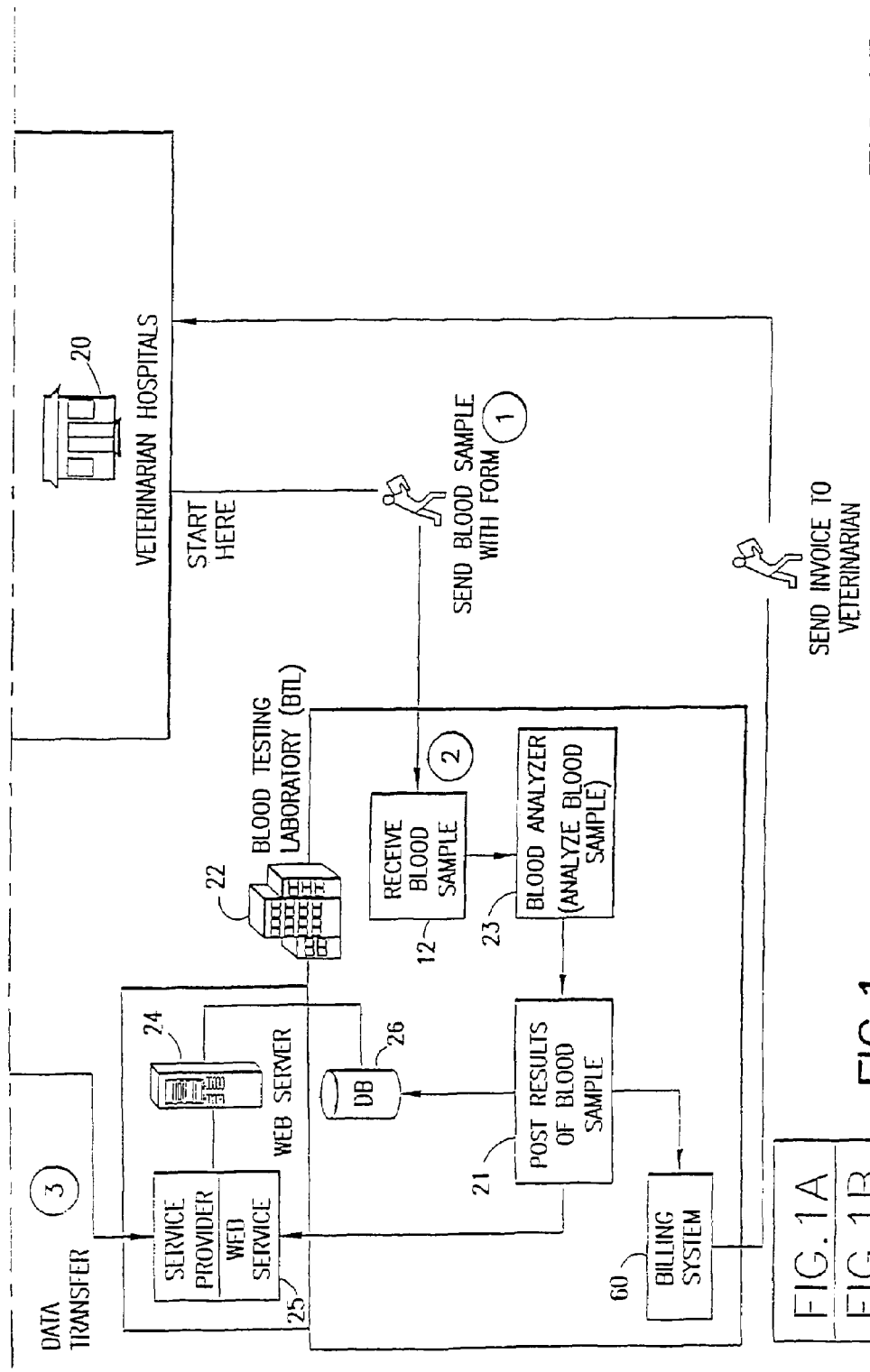

METHODS AND SYSTEMS FOR PROVIDING A NUTRACEUTICAL PROGRAM SPECIFIC TO AN INDIVIDUAL ANIMAL

This application is a continuation-in-part of commonly-owned, U.S. patent application Ser. No. 12/157,106 filed on Jun. 6, 2008, which is a divisional of U.S. patent application Ser. No. 11/228,571 filed on Sep. 15, 2005 (now U.S. Pat. No. 7,409,297 issued on Aug. 5, 2008), and which claims the benefit of U.S. Provisional Patent Application No. 60/610,748, filed Sep. 17, 2004, each of which is incorporated herein and made a part hereof by reference.

BACKGROUND OF THE INVENTION

The present invention relates to methods and systems for providing a nutraceutical program specific to an individual animal. More particularly, the present invention enables an assessment of the health of internal organs of an animal, and the available vitamins, minerals and enzymes required for the metabolic processes. Using blood results and medical history, the Nutritional Blood Test (NBT) provided by the present invention prioritizes the nutrients required to optimize organ function and balance metabolism. It then matches the results to specific nutraceuticals that support a clinical response.

An animal's organs and glands, though not considered pathological, may nonetheless be functioning less than optimally. There may be underlying weaknesses, deficiencies or imbalances, which if left unchecked, may degenerate into a disease process.

Standard blood testing focuses strictly on pathology and often fails to expose metabolic and physiological weaknesses. While blood testing is customarily the first step toward diagnosis, the need exists for an analysis that distinguishes organ weaknesses rather than simply identifying "normals" and "abnormals." The orientation needs to be expanded from "what organs are not functioning" to "how the organs should be functioning."

In the past, the standard treatment was to provide medical and nutritional supplements to animals to maintain or restore their health. One prior art method of providing nutraceuticals to animals is in the form of multivitamins wherein a predetermined amount of nutritional supplements are administered, without variation, for a given set of animals. In such a method, the specific nutritional deficiencies of the individual animal are not addressed.

Other prior art methods have been developed for providing nutritional supplements to animals. However, none of these prior art methods provide for analyzing an animal and prescribing a nutraceutical program specifically tailored for that particular animal based on the analysis. In particular, the prior art does not provide for prescribing a nutraceutical program specifically tailored to address deficiencies of an animal, in terms of identifying desired nutraceuticals and calculating dosages for the identified nutraceuticals for treating such deficiencies in order to optimize the health of the animal. Further, the prior art does not disclose a method for optimizing the health of an animal which has blood scores in the normal range but which may still have some specific inadequacies.

Accordingly, there is a need in the art for more refined methods and apparatus that can determine specific nutritional deficiencies of an animal that tests within a "normal" range. Therefore, it is an object of the present invention to provide methods and systems for customized treatment of animals. It is another object of the present invention to provide methods and systems for customized treatment of animals based on blood analysis. It is a further object of the present invention to provide methods and systems of treating animals, tailored to individual animals, based on blood analysis of the animals. It is an additional object of the present invention to provide methods and systems for treating animals that may lack certain nutrients. It is still a further object of the present invention to provide methods and systems for treating animals that have organs that are not functioning optimally.

It is an additional object of the present invention to provide methods and systems for treating animals, which tailors composition and dosages of neutraceuticals to the specific needs of an individual animal. It is still a further object of the present invention to provide methods and systems for veterinarians to forward an animal's blood work to a lab, and in response thereto, to receive a treatment recommendation. It is a further object of the present invention to provide methods and systems which enable a veterinarian to interact with a provider of nutraceutical treatment plans via a communications network, such as the Internet.

The methods and systems of the present invention provide the foregoing and other advantages.

SUMMARY OF THE INVENTION

The present invention relates to methods and systems for providing a nutraceutical program specific to an individual animal. The present enables a detailed assessment of the health of internal organs of an animal, as well as the available vitamins, minerals and enzymes required for the metabolic process. The methods and systems of the present invention prioritize the nutrients required to optimize organ function and to balance metabolism. The present invention identifies the specific nutraceuticals, and determines specific dosages thereof, in response to the assessment. The present invention is useful in identifying the deficiencies or imbalances of an animal due to poor nutrient absorption and utilization, and provides a treatment responsive thereto, specifically tailored to an individual animal.

In an example embodiment of the present invention, a method of providing a nutraceutical program specific to an individual animal is provided. Blood is drawn from the animal and analyzed at a lab to obtain blood test results. The blood test results are scored to obtain at least one blood test score for at least one corresponding blood parameter. It can then be determined whether the at least one blood test score falls outside a normal range defined for the corresponding blood parameter. An optimal range within the normal range is also defined for each blood parameter. If the blood test score(s) for the at least one corresponding blood parameter are within the optimal range(s), the animals health is optimal and no nutraceuticals are prescribed for the animal.

If the at least one blood test score falls within the normal range but outside of the optimal range, one or more nutraceuticals needed to bring the animal within the optimal range for the at least one corresponding blood parameter are identified. A prescribed dosage amount is then calculated for at least one of the one or more identified nutraceuticals for the animal. The calculation of the prescribed dosage amount is based on at least the blood test score for the corresponding blood parameter and a deviation of the blood test score from the optimal range.

If the at least one blood test score falls outside of the normal range, it is determined that the animal is ill, and standard nutrients or medications are prescribed in order to bring the at least one blood test score within the normal range.

In one example embodiment, the animal may comprise a human. In another example embodiment, the animal may comprise a fish, an amphibian, a reptile, a bird, or a mammal. Alternatively, the may belong to one of the following groups of animals: livestock, cattle, pets, domesticated animals, zoo animals, or exotic animals.

The identification of the one or more nutraceuticals may be based on at least one of animal type, animal physiology, animal biochemistry, data describing an observed physical condition of the animal, data describing a medical diagnosis of the animal, and the like.

The calculation of the prescribed dosage amount for a particular identified nutraceutical may comprise calculating a "pre-cap" dosage amount based on the blood test score, the deviation of the at least one blood test score from the optimal range, animal type, animal weight, dosage strength information, and dosage limit information. The calculated pre-cap dosage amount may then be compared to a "low-cap" dosage amount and a "high-cap" dosage amount for the particular animal. If the pre-cap dosage amount is between the low-cap and high-cap dosage amounts, the prescribed dosage amount is equal to the pre-cap dosage amount. If the pre-cap dosage amount is greater than the high-cap dosage amount, the prescribed dosage amount is equal to the hi-cap dosage amount. If the pre-cap dosage amount is less than the low-cap dosage amount, the prescribed dosage amount is equal to the low-cap dosage amount.

The low-cap dosage amount is the minimum amount of an identified nutraceutical prescribed for an animal regardless of the animal weight or the deviation of the at least one blood test score from the optimal range. The high-cap dosage amount is the maximum amount of an identified nutraceutical prescribed for an animal regardless of the animal weight or the deviation of the at least one blood test score from the optimal range.

In one example embodiment of the present invention, the pre-cap dosage amount may be equal to a dosage strength S times the weight of the animal. The dosage strength S may be defined as:

$$S = \text{slope}(\text{blood score} - \text{maximum range value}) + \text{High dosage}.$$

A plurality of severity levels indicating a range of blood test scores which deviate from the optimal range may be established. A negative severity level may indicate a range of blood test scores below a minimum of the optimal range, and a positive severity level may indicate a range of blood test scores above a maximum of the optimal range.

If the at least one blood test score falls within a negative severity level, then the maximum range value is the highest value of the negative severity level closest to the optimal range and a minimum range value is the lowest value of the negative severity level furthest from the optimal range. If the at least one blood test score falls within a positive severity level, then the maximum range value is the highest value in the positive severity level furthest from the optimal range and the minimum range value is the lowest value in the positive severity level closest to the optimal range.

The slope may then be defined as:

$$\text{slope} = (\text{high dosage} - \text{low dosage})/(\text{maximum range value} - \text{minimum range value}).$$

The low dosage may indicate a minimum nutraceutical strength prescribed for an animal regardless of the animal weight or the severity level of the at least one blood test score. The high dosage may be approximately double the low dosage.

At least one of the normal range and the optimal range may be derived from a database containing historical blood test scores for a plurality of animals. The database may be updated with information regarding the animal type, the animal weight and the blood test scores.

The blood parameters measured in the blood test analysis may comprise at least one of white blood cell information, red blood cell information, and blood chemistry information. The blood parameters may correspond to the function of one or more organs of the animal. For example, the blood parameters measured during the blood test may include one or more of the following: AST (SGOT), ALT (SGPT), total bilirubin, alkaline phosphatase, GGTP, total protein, albumin, globulin, A/G ratio, cholesterol, urea nitrogen (Bun), creatinine, BUN/creatinine ratio, phosphorus, calcium, glucose, amylase, lipase, sodium, potassium, chloride, CPK, triglycerides, lactic dehydrogenase, white blood cell count, red blood cell count, hemoglobin (HGB), hemactocrit (PCV, HCT), absolute polys (neutrophils), absolute lymphocytes, absolute monocytes, absolute eosinophils, platelet count, T4, and the like.

The nutraceuticals may comprise at least one of vitamins, minerals, enzymes, amino acids, homeopathic supplements, herbal supplements, raw glandular supplements, and the like.

The blood test results may be electronically communicated from the lab to a service provider. The service provider may score the blood test results to obtain the at least one blood test score. The service provider may also calculate the prescribed dosage amounts of the identified nutraceuticals. The prescribed dosage amounts may be electronically communicated from the service provider to a compound pharmacist. The compound pharmacist may then prepare a prescription containing the one or more identified nutraceuticals in accordance with the prescribed dosage amounts and ship the prescription to an owner of the animal or veterinarian for administration to the animal.

The present invention also provides for systems for implementing the above-described methods. In particular, the present invention encompasses a system for providing a nutraceutical program specific to an individual animal. In an example embodiment of such a system in accordance with the present invention, a blood analyzer is provided for analyzing a blood sample of an animal to obtain blood test results. In addition, a database is provided which contains historical blood test scores for a plurality of animals. The historical blood test scores define normal ranges for corresponding blood parameters and define corresponding optimal ranges within the normal ranges for the corresponding blood parameters. A processor in communication with the blood analyzer and the database is also provided as part of the system. The processor may be adapted to: score the blood test results to obtain at least one blood test score for at least one corresponding blood parameter and determine if the at least one blood test score falls outside the normal range defined for the corresponding blood parameter. If the at least one blood test score falls within the normal range but outside of the optimal range, the processor may identify one or more nutraceuticals needed to bring the animal within the optimal range for the at least one corresponding blood parameter. Once the nutraceutical(s) are identified, the processor may then calculate a prescribed dosage amount for at least one of the one or more identified nutraceuticals for the animal. The calculation of the prescribed dosage amount may be based on at least the blood test score for the corresponding blood parameter and a deviation of the blood test score from the optimal range.

If the at least one blood test score falls outside of the normal range, it is determined that the animal is ill, and standard nutrients or medications are prescribed for the animal in order to bring the at least one blood test score within the normal range.

The processor identifies one or more nutraceuticals based on at least one of animal type, animal physiology, animal biochemistry, data describing a physical condition of the animal, and data describing a medical diagnosis of the animal. The data used by the processor may be obtained from the database or input via a user terminal, such as a personal computer, personal digital assistant, cellular telephone, laptop computer, or the like. Such data may be directly input via a user terminal directly connected to the processor or via a user terminal remotely linked to the processor via a wired or wireless communication network, such as the Internet, a wide area network, a local area network, a global area network, a telephone network, or the like, including any combination of such networks. Those skilled in the art will appreciate that the processor may also be in communication with more than one database containing the required information.

The processor may calculate the prescribed dosage amount for a particular identified nutraceutical using the formulas arid methods discussed above.

The database(s) may also store information regarding the severity levels discussed above, which indicate ranges of blood test scores which deviate from the optimal range (e.g., the negative and positive severity levels discussed above).

The blood test results may be electronically communicated from the blood analyzer at a lab to the processor at a service provider. The prescribed dosage amounts calculated by the processor may then be electronically communicated from the service provider to a compound pharmacist. The compound pharmacist can then prepare a prescription containing the one or more identified nutraceuticals in accordance with the prescribed dosage amounts and ship the prescription to an owner of the animal or a veterinarian for administration to the animal.

The features discussed above in connection with the example embodiments of the methods of the present invention are equally applicable to the system embodiments of the present invention.

BRIEF DESCRIPTION OF THE DRAWINGS

The present invention will hereinafter be described in conjunction with the appended drawing figures.

DETAILED DESCRIPTION

Figure 1A:
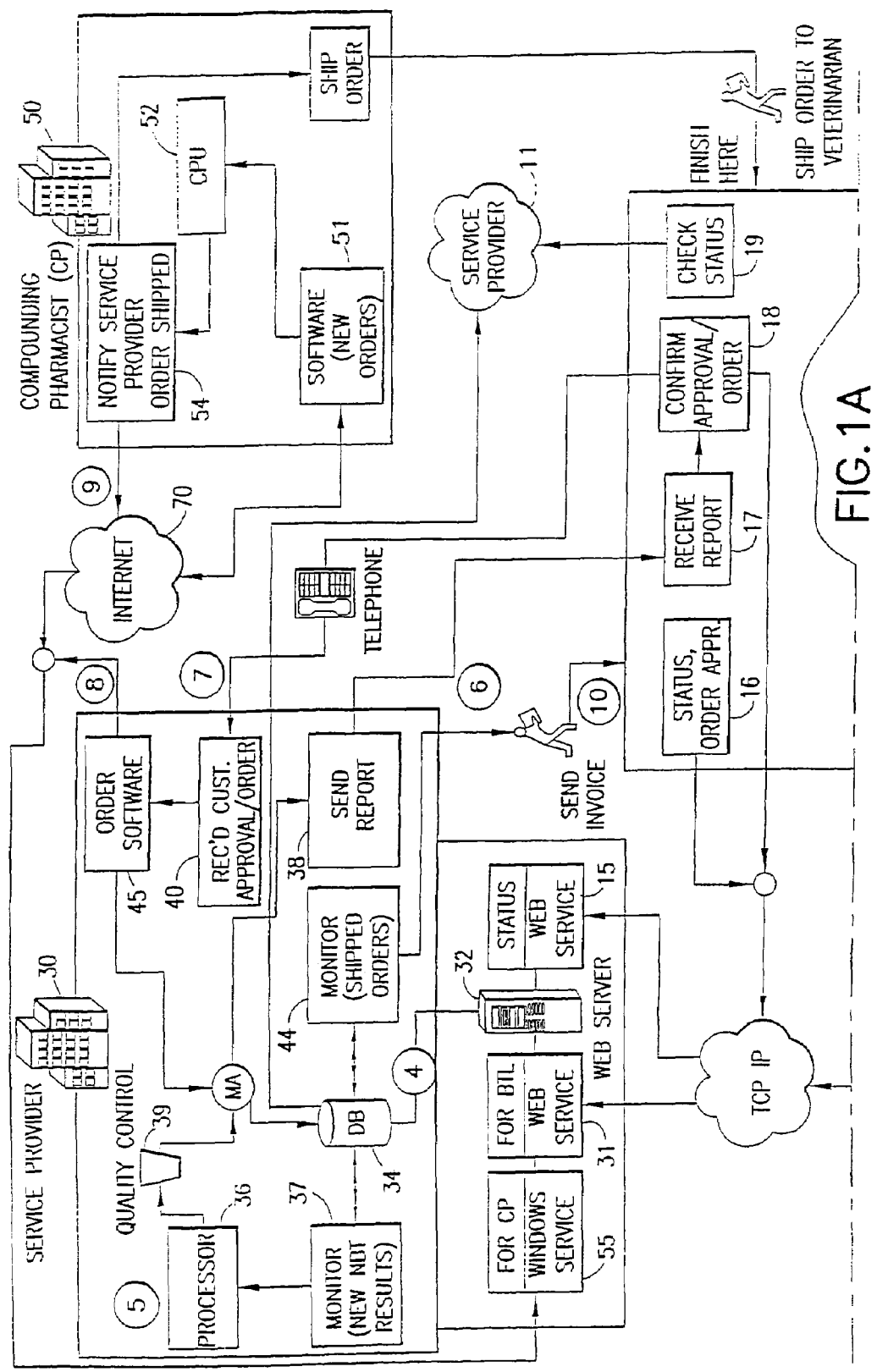
FIG. 1 (FIGS. 1A and 1B) shows a block diagram of an example embodiment of the present invention.

The ensuing detailed description provides exemplary embodiments only, and is not intended to limit the scope, applicability, or configuration of the invention. Rather, the ensuing detailed description of the exemplary embodiments will provide those skilled in the art with an enabling description for implementing an embodiment of the invention. It should be understood that various changes may be made in the function and arrangement of elements without departing from the spirit and scope of the invention as set forth in the appended claims.

The present invention provides methods and systems for providing a nutraceutical program specific to an individual animal. In accordance with an example embodiment of the present invention, an animal's blood is taken and an analysis is performed thereon. The blood test is scored to determine whether it is normal or abnormal. An abnormality is normally indicative of a disease. In response to an abnormality, "off-the-shelf" nutrients, typically in the form of capsules, are provided for the animal. Results for an animal in the normal range are analyzed to determine whether there are any nutritional deficiencies. With this process, treatments are tailored to the individual animal in terms of the nutraceuticals to be taken by the animal.

In one example embodiment, the animal may comprise a human. In another example embodiment, the animal may comprise a fish, an amphibian, a reptile, a bird, or a mammal. Alternatively, the may belong to one of the following groups of animals: livestock, cattle, pets, domesticated animals, zoo animals, or exotic animals. The methods and systems of the present invention can be adapted for use with most animal types.

There are typically ranges of blood test scores for each measured blood parameter that are suitable for a healthy (i.e., "normal") animal. However, within these normal ranges, there are subtle gradations of tissue integrity and organ efficiency that can be measured and that are an important component of wellness and healing. The present invention looks beyond the reference range (normal range) to a level or measurement that highlights how an organ or system is performing. In other words, the present invention enables the selection of nutrients for optimizing overall health and organ function for even a healthy animal.

Essentially, the present invention seeks to provide treatment to bring an animal into an optimal range, which exists within a normal reference range. The optimal range is defined as the more narrow normal range in which organs or metabolic processes are functioning at peak efficiency. Within the optimal range there is no degradation and no need for corrective measurements. However, results outside the optimal range, while not necessarily indicating a disease or abnormality, do indicate that a particular organ system may not be functioning at optimal efficiency and therefore, may require corrective support.

The blood test results of an animal are analyzed and it is determined whether the blood test scores fall within the optimal ranges established for particular blood parameters. An assessment is made of the status of specific organs, along with a determination of stored and available levels of vitamins, minerals and enzymes. In response to these results, a nutritional program specific to the animal is recommended for the animal.

The nutrients or nutraceuticals considered for use in connection with the present invention may include vitamins, minerals, enzymes, amino acids, homeopathic supplements, herbal supplements, raw glandular supplements, and the like. These nutrients are specifically blended to match the deficiencies found in the animal's blood and are precisely dosed according to the animal's weight and severity of the imbalances or deficiencies. The nutrient combination may be provided in powder or liquid form as desired. Providing such custom tailored dosages eliminates the need for pre-formulated capsules and tablets, and ends the challenges of administering multiple tables and capsules. When necessary or at the request of the attending veterinarian, the nutrient combination can be made up in capsule or tablet form. Additionally, inert compounds, such as binders, fillers, coatings, preservatives, coloring agents and additives, which often increase the risk of intestinal inflammation or interference with the absorption of fat-soluble vitamins, are eliminated by the present invention. Advantageously, custom blended powders are more bio-available and thereby maximize assimilation and minimize gastrointestinal discomfort. Further, overdosing is eliminated, as precise quantities are provided.

From the perspective of a veterinarian, the present invention may involve the following steps:

1. Drawing blood for a Complete Blood Count (CBC), Super Chem blood test (also referred to as the complete blood chemistries, SMA, or CHEM Profile), and a Thyroid Test (T4), or the like;

2. Completing a questionnaire and affixing tracking stickers from a Blood Testing Laboratory Diagnosis (Request or Accession) Form to the blood vials;

3. Scheduling pick-up of the blood by a Blood Testing Laboratory;

4. Receiving a report from the lab highlighting imbalances and/or deficiencies, and outlining the recommended responsive therapy; and 5. Receive prescribed dosages of nutraceuticals from compound pharmacist.

From the perspective of the service provider that provides the Nutritional Blood Test of the present invention, the blood testing lab and the compound pharmacist center, the present invention may involve the following steps:

1. Receiving a blood sample from an animal with the corresponding medical history of the animal including age, sex, breed, weight, current medications, supplementation and diet, vaccination history, medical diagnosis information, and the like;

2. Analyzing the blood specifically for information relating to the red blood cells, white blood cells and blood chemistries;

3. Scoring the blood; which may include taking the results of at least one of a Complete Blood Count (CBC), a Super Chem blood test (also referred to as the complete blood chemistries, SMA, or CHEM Profile), a Thyroid Test (T4), or the like, and scoring the results of one or more of these tests in relationship to a deviation from optimal;

4. Comparing the scores to a database:

5. Determining if and where the scores deviate from optimal;

6. Determining the nutraceuticals needed (as determined from the physiological analysis of the blood with the end goal of bringing the animal to optimal); and 7. Determining proper dosage (of nutrients, nutraceuticals and remedies) for the animal; and 8. Utilizing a Compounding Pharmacist, preparing proper dosages of specific nutraceuticals specifically tailored to the animal.

The term "nutraceuticals" as used herein is meant to encompass vitamins, minerals, glandular supplements, medicinals, enzymes, amino acids, nutrients, homeopathic supplements, herbal supplements, and the like. The nutraceuticals may generally be prescribed on two to three month supplemental programs (for severe cases, week-to-week or monthly regimens are prescribed). After the initial period, the blood test(s) may be repeated and a follow-up analysis may be performed. The deficiencies and imbalances are re-evaluated and compared to the original NBT analysis and, based upon the progress, the supplementation program is adjusted. (Either enhanced, kept the same, or reduced to a maintenance level based upon the blood results and the animal's clinical condition and level of improvement.)

As a result of looking up blood scores manually and prescribing supplements to correct deficiencies over approximately the past 25 years, data has been correlated and a computer model has been developed. In a preferred embodiment, the computer analysis provided by the present invention evaluates approximately 36 different blood score factors and compares them to reference ranges developed over years of testing. The optimal ranges of the present invention are developed from this historical data, based upon the clinical importance of the individual blood test and what the blood test indicates physiologically and biochemically. The present invention then factors in characteristics about the animal such as size and weight and creates an individual treatment program for an animal, which identifies nutrients and dosages. The treatment program is therefore specifically customized for the animal and the animal is provided with exactly the treatment needed to optimize the animal's health.

FIG. 1 is a block diagram of an example embodiment of the present invention. Initially, a veterinarian submits a blood sample (shown at 1) from a veterinarian hospital 20 to a blood testing laboratory 22. The blood sample submission 1 is received at the blood testing laboratory 22(shown at 2). The received blood sample 2 from the veterinarian may be labeled for identification and tracking purposes at a receiving station 12. The blood sample submission 1 may be accompanied by an NBT (Nutritional Blood Test) Questionnaire developed in accordance with the present invention. Alternatively, the blood testing laboratory 22 may send the NBT Questionnaire or Blood Test Request or Accession Form to the veterinarian hospital 20 by fax or otherwise. The NBT Questionnaire includes specific information about the animal, including but not limited to the Weight, Age, Sex Breed, Species, and clinical and medical history concerning the animal. Once the veterinarian has provided the completed NBT Questionnaire, the Questionnaire is labeled at the Blood Testing Laboratory and is kept with the blood vials that were submitted. Tracking stickers may be provided on the Questionnaire, which tracking stickers can be affixed to the blood vials for tracking purposes.

The blood testing laboratory 22 performs a blood analysis (e.g., at blood analyzer 23) pursuant to the present invention and the results can be printed and/or sent or faxed to the veterinarian. The results of the blood test are posted (shown at 21). The Report sent to the veterinarian may include the blood results of at least one of a Complete Blood Count (CBC), Super Chem blood test (or the complete blood chemistries), and a T4 test for the veterinarian's medical evaluation. The results of the test(s) and corresponding paperwork including the NBT Questionnaire are also stored on a database 26 at the blood testing laboratory 22, which is in communication with server 24 located at the blood testing laboratory 22. At designated intervals, a web service 25 (operated by the service provider 30) polls this server 24 to check for new data. When a new test is found, the data is then encrypted and transferred (shown at 3) (e.g., using TCP/IP) to a web service 31 on the main server 32 at the service provider 30 (e.g., such as Bionutrional, LLC, the assignee of the present invention) at which point the data is unencrypted and transferred (shown at 4) to and stored in the primary database 34 located at the service provider 30. Those skilled in the art will appreciate that, although FIG. 1 shows a database 26 located at the blood testing laboratory 22 and a database 34 located at the service provider 30, the functions of these two databases may be combined into a single database, which may be located at a remote location with a corresponding database server, or at either the service provider 30 or the blood testing laboratory 22. In either case, the blood testing laboratory 22 and/or the service provider 30 may communicate with such a combined database via conventional methods, such as via the Internet using a web browser, or over a local area network or a wide area network, as is known in the art.

A monitoring device 37 monitors new data loaded into the service provider database 34, and triggers an event, which notifies the service provider 30 that a new blood test has been sent from the blood testing laboratory 22. Thereafter, based upon the NBT Questionnaire (medical history, diagnosis and drugs being used) and the physiological analysis of the blood, the service provider 30 conducts a nutritional and physiological analysis (e.g., at processor 36) to determine the optimum range and the selection and calculation of the specific nutraceuticals that will be custom blended for the animal. It should be appreciated that the processor 36 selects a particular nutraceutical or nutraceuticals for each blood parameter based on a number of factors, which factors include but are not limited to the severity of the deficiency, the type of animal, the sex of the animal, the weight of the animal, historical treatment data, known associations between specific nutraceuticals and blood parameters, physiological data obtained from the blood analysis, animal physiology, animal biochemistry obtained from the blood analysis, data describing an observed physical condition of the animal, data describing a medical diagnosis of the animal, and the like. This selection process may be governed by "rules" which enable the processor 36 to take into account the foregoing factors when selecting a particular nutraceutical. Further, the rules and the inter-relationships between the particular factors used are continuously updated based on new data acquired through the testing and monitoring enabled by the present invention, such that the processor 36 is able to continually refine the selection process over time.

The calculated prescription may forwarded for review and approval (shown at 5) to a quality control station 39 at the service provider 30. A report containing the blood results, interpretation of the results, recommended therapy (e.g., nutraceutical dosages and schedule for administration of same), follow-up schedule and order form is then communicated (shown at 6) to the veterinarian for review by communications means 38, for example via the Internet 70, email, regular mail, or any other communication means and received by corresponding communication means 17 at the veterinarian hospital 20. Order approval can also be sent and order status checked by communication device 16 at the veterinarian hospital, which is in communication with the web service 31 of the service provider 30.

Upon receiving approval 40 of the Report from the veterinarian hospital 20 (via telephone, Internet, facsimile, email, or any other communications means 18), the veterinarian places an order (shown at 7) with the service provider. An order is generated through software 45 (referred to Nutritional Therapy Processing System software) at the service provider 22 and a notification (shown at 8) of the order is sent to the Compounding Pharmacist 50 that an order has been placed and is ready for processing. The Compounding Pharmacist 50 utilizes the corresponding software 51 to view the order. The compound pharmacist 50 may be in communication with the service provider 30 via communication means 54 and Windows Service 55. After processing the order (e.g., at CPU 52), the Compounding Pharmacist 50 sends a notification (shown at 9) to the service provider 30 via communication means 54 that the order has been shipped and is ready for invoicing. The service provider 30 monitors shipped orders (e.g., at monitor 44) and generates an invoice (shown at 10) which is sent to the veterinarian hospital 20. The blood testing laboratory 22 may also generate an invoice for the blood testing services provided (e.g., via billing system 60) and send this invoice directly to the veterinarian hospital 20. Alternatively, the blood testing laboratory 22 may bill the service provider 30, who in turns passes the costs of the blood test on to the veterinarian hospital 20 in the invoice shown at 10.

At any time, veterinarians can log into the service provider web site 11, access their own private area where they can view their patient's NBT reports, check the status of orders 19 and view a history of their orders and reports. A Status Web Service 15 connected to server 32 enables the veterinarian to obtain status information on orders. In the public area of the website, visitors can find out more about the Nutritional Blood Test and integrating nutrition with patient care.

Those skilled in the art will appreciate that the example described above and shown in FIG. 1 is only one example implementation of the present invention, and that the entire process encompassed by the present invention may be implemented by a single service provider at a single location. In other words, the service provider may provide veterinary services, blood testing services, blood analysis, the determination of required nutraceuticals, the determination of prescribed dosages, and compounding pharmacist's services at a single location. Alternatively, the steps of the present invention may be provided by one or more entities or individuals at one or more distributed locations. These locations may be interconnected by a network, such as one or more of a telephone network, the Internet, a local area network, a wide area network, a wired or wireless network, or any combination thereof.

Figure 2:
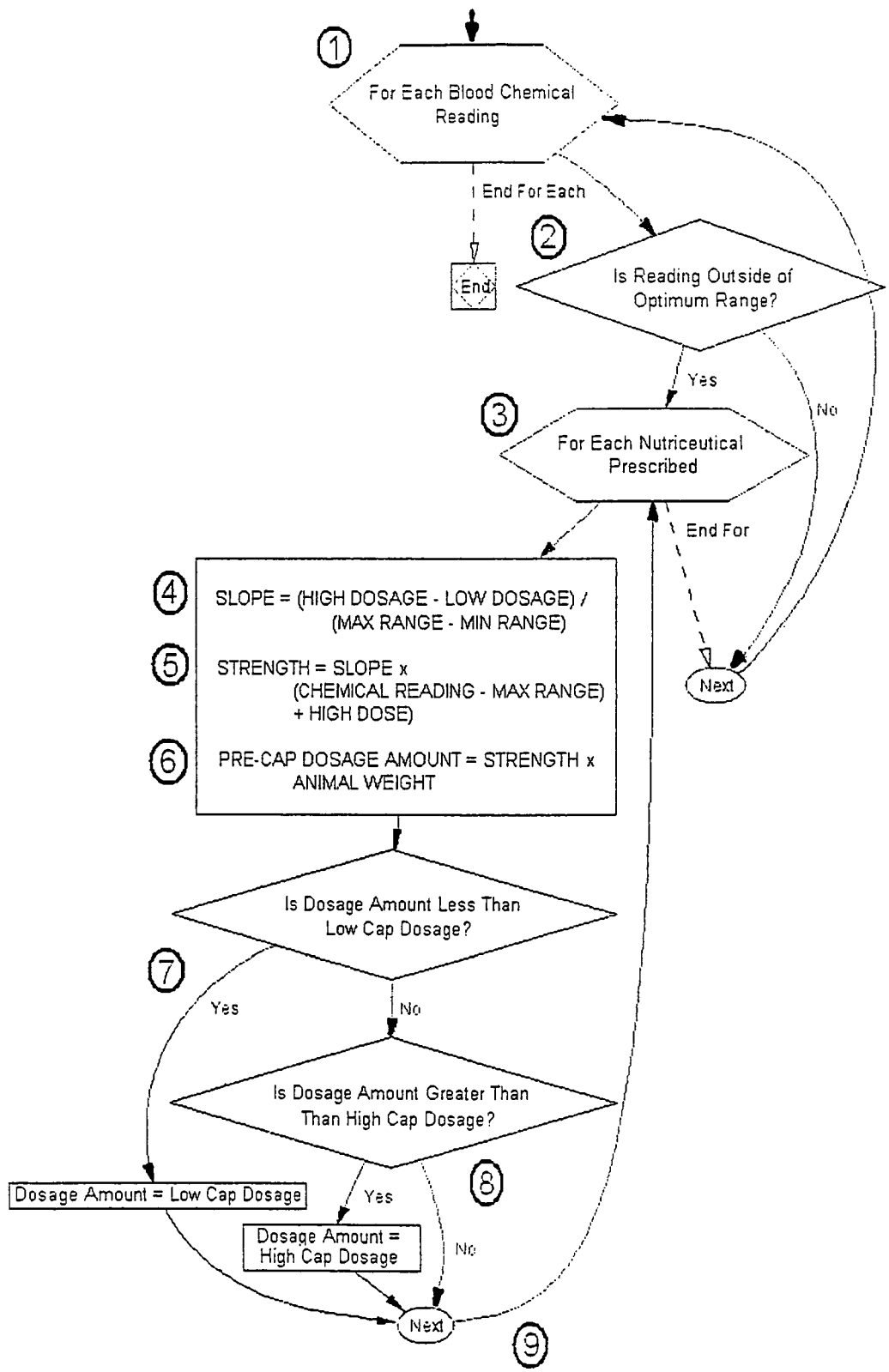
FIG. 2 shows a flow chart of an example embodiment of a Nutraceutical Generation Process used in connection with the present invention.

FIG. 2 shows a flowchart of an example embodiment of the Nutraceutical Generation Process of the present invention, which determines the proper dosages for each nutraceutical prescribed. The process begins with blood chemical readings (step 1) that are the result of tests that are conducted for numerous blood score factors. A sample of blood test scores for various blood test parameters is shown in Table 1 below. The example scores shown in Table 1 are for a canine blood sample. Table 1 shows the actual breakdown of the individual blood scores for each measured blood parameter as they deviate from an optimum range will determine what they will mean nutritionally. Each blood score is compared with the normal and optimal ranges determined for that particular blood parameter.

TABLE 1

Sample Blood Test Scores for Canine

| Blood Parameters (Chemistries) | Outside Normal | Normal Not Optimal | Optimal | Reference Range | Optimum Range |
|---|---|---|---|---|---|
| AST (SGOT) | | | 43 | 15-66 | 28-53 |
| ALT (SGPT) | 126 | | | 12-118 | 39-77 |
| Total Bilirubin | | | 0.2 | 0.1-0.3 | 0.1-0.3 |
| Alkaline Phosphatase | 664 | | | 5-131 | 37-100 |
| GGTP | | 7 | | 1-12 | 3-4.5 |
| Total Protein | | | 6.7 | 5-7.4 | 6-6.8 |
| Albumin | | 2 | | 1.6-6.0 | 2.7-3.6 |

TABLE 1-continued

Sample Blood Test Scores for Canine

| Blood Parameters (Chemistries) | Outside Normal | Normal Not Optimal | Optimal | Reference Range | Optimum Range |
|---|---|---|---|---|---|
| Globulin | | | 2.8 | 1.6-3.6 | 2.1-3.1 |
| A/G Ratio | | | 1.4 | 0.8-2 | 1.1-1.7 |
| Cholesterol | | 300 | | 92-324 | 135-266 |
| Urea Nitrogen (BUN) | | 23 | | 6-25 | 14-19 |
| Creatinine | 1.8 | | | 0.5-1.6 | 0.8-1.3 |
| BUN/Creatinine Ratio | | | 13 | 4-27 | 10-21 |
| Phosphorus | | | 4.9 | 2.5-6 | 3.4-5.1 |
| Calcium | | | 10.1 | 8.9-11.4 | 9.5-10.8 |
| Glucose | | | 79 | 70-138 | 70-183 |
| Amylase | | 969 | | 290-1125 | 499-916 |
| Lipase | | | 420 | 77-695 | 232-541 |
| Sodium | | | 150 | 139-154 | 143-150 |
| Potassium | 5.6 | | | 3.6-5.5 | 4.1-5 |
| Chloride | | | 109 | 102-120 | 107-116 |
| CPK | | 155 | | 59-895 | 268-686 |
| Triglycerides | | | 147 | 29-291 | 95-226 |
| Lactic Dehydrogenase | | | 180 | 20-500 | 140-380 |
| WBC (White Blood Cells) | | | 11.9 | 4-15.5 | 6.9-12.6 |
| RBC (Red Blood Cells) | | 5.3 | | 4.8-9.3 | 5.93-8.18 |
| Hemoglobin (HGB) | | 12.8 | | 12.1-20.3 | 14.2-18.3 |
| Hematocrit (PCV, HCT) | | 38 | | 36-60 | 42-54 |
| Absolute Polys (Neutrophils) | | | 7259 | 2060-10600 | 4195-8465 |
| Absolute Lymphocytes | | | 2380 | 690-4500 | 1643-3548 |
| Absolute Monocytes | | 833 | | 0-840 | 210-790 |
| Absolute Eosinophils | 1428 | | | 0-1200 | 50-900 |
| Platelet Count | | 389 | | 170-400 | 228-343 |
| T4 | | | 1.87 | 1-4 | 1.6-4 |

Note that the optimal range for glucose is 70-183, while the normal range for glucose is 70-138, which is the only parameter for which the optimal range is outside of the normal range. The normal range for glucose is set outside of the normal range on the high end to compensate for elevated glucose levels present in the blood immediately after eating.

From Table 1 it can be seen that the blood test scores for albumin, urea nitrogen (BUN), creatinine, alkaline phosphatase, ALT (SGPT), cholesterol, potassium, amylase, CPK, GGTP, hemoglobin (HGB), hematocrit (PVC, HCT), red blood cell count, absolute monocytes, absolute eosinophils, and platelet count fall either within the normal range but outside of the optimal range or fall outside of the normal range altogether. The remaining measured blood parameters in the Table 1 example fall within the optimal range. The scores for the blood parameters that fall outside of normal (ALT (SGPT), alkaline phosphatase, creatinine, potassium, and absolute eosinophils) may be indicative of a disease and may be treated with prescription medications. An interpretation of the blood test scores of Table 1 that fall outside the optimal and normal ranges is provided below.

The blood test score for albumin is 2, which is normal but below optimum. A depressed ALBUMIN level may indicate insufficient or poor quality protein in the diet. It may also indicate a degenerative disease and wasting or a sluggish metabolism of the liver. This often indicates the requirement for liver supplements, certain B vitamins, Vitamins A, C, and D, amino acids, and lecithin.

The blood test score for urea nitrogen (BUN) is 23, which is normal but above optimal. An elevated BUN level indicates an overload of the liver and kidneys as well as weaknesses in the pituitary, thyroid and liver, which oversee protein metabolism. This overload may indicate a deficiency of important minerals such as magnesium, copper, iodine and iron. It may also indicate serious kidney disease.

The blood test score for creatinine is 1.8, which is above the normal range. An elevated creatinine level indicates impaired metabolism in the muscles as well as improper protein absorption. This may indicate weaknesses in the pancreas leading to low levels of pancreatic enzymes as well as weaknesses in the anterior pituitary and gonadal system. This may also indicate serious kidney disease.

The blood test score for alkaline phosphatase is 664, which is above the normal range. An elevated alkaline phosphatase level indicates the inefficient movement of minerals throughout the body. This may indicate that the glands are too acidic as compared to the blood. This may also indicate hyperactivity and an underlying weakness in the adrenals and the gonadal system. It may also indicate the requirement for acidic nutrients such as vitamin C (ascorbic acid), PABA, pantothenic acid, and folic acid as well as important minerals, sodium and potassium. Long standing elevated levels can be associated with weaknesses of the adrenal glands (called Cushing's Disease) as well as the presence of serious degenerative disease such as cancer. Elevated levels are common in rapidly growing kittens and puppies, or when a fractured bone is healing.

The blood test score for ALT (SGPT) is 126, which is above the normal range. An elevated alanine transferase level may indicate a weakness or disease of the liver. This also may indicate deficiencies of vitamin A, vitamin D and vitamin B6 as well as iron, copper and iodine. Elevated levels may also indicate an exposure to toxic chemicals or pollutants.

The blood test score for cholesterol is 300, which is normal but above optimal. An elevated cholesterol level may indicate higher than desired levels of saturated fats in the diet (as found in most commercial pet foods). These saturated fats stimulate the absorption of all fats in general, including cholesterol. This may cause the blood to thicken and predispose oxidation of these blood fats (rancidity). This indicates the need for lecithin, choline and inositol and trace and essential minerals. This may also indicate an overall weakness in the anterior pituitary as well as an imbalance in the acid levels of the stomach and intestines.

The blood test score for potassium is 5.6, which is above the normal range. An elevated potassium level may indicate a weakness as well as excessive breakdown of heart muscles, which may lead to irregular contractions. This may indicate the requirement for vitamin E, coenzyme Q10 and the amino acid L-carnitine.

The blood test score for amylase is 969, which is normal but above optimal. An elevated amylase level indicates an active inflammation in the pancreas, which may represent a weakened pancreas or in some cases may require medical treatment (acute pancreatitis). Diet should be adjusted to lower intake of fat, and to properly balance the levels of essential fatty acids, highly digestible proteins and complex carbohydrates.

The blood test score for CPK is 155, which is normal but below optimal. A depressed creatine phosphokinase level may indicate atrophy or wasting of the muscles, including the muscles. of the heart. This may also indicate deficiencies of essential amino acids and vitamin E.

The blood test score for GGTP is 7, which is normal but above optimal. An elevated gamma glutamyl transferase level indicates a decrease in oxygen levels in the body due to the presence of excessive wastes and toxins. This may indicate deficiencies of vitamin B complex, copper and iron. This may also indicate weaknesses in the liver.

The blood test score for hemoglobin (HGB) is 12.8, which is normal but below optimal. A depressed hemoglobin level indicates anemia, malnutrition and/or improper absorption of food into the blood. This may indicate weaknesses in the liver and spleen as well as deficiencies of vitamin B complex, vitamin C and iron as well as the requirement for highly-digestible proteins and amino acids.

The blood test score for Hematocrit (PCV, HCT) is 38, which is normal but below optimal. A depressed hematocrit level indicates less than desired levels of red blood cells (anemia). This may indicate weaknesses in the bone marrow, liver and spleen, as well as deficiencies of vitamin B12 and iron.

The blood test score for RBC (Red Blood Cells) is 5.3, which is normal but below optimal. A depressed red blood cell count indicates a loss of blood or the body's inability to manufacture adequate levels of red blood cells (anemia). This may indicate higher than desired levels of wastes or toxins in the blood, an adverse reaction to drugs, or the presence of a chronic degenerative condition. This may also indicate weaknesses in the liver, bone marrow, spleen and liver as well as the requirement for vitamin B12, chlorophyll and iron.

The blood test score for Absolute Monocytes is 833, which is normal but above optimal. An elevated monocyte count indicates the presence of longer-standing infection and inflammatory processes. This may indicate the requirement for vitamin C, vitamin A and vitamin E.

The blood test score for Absolute Eosinophils is 1428, which is above normal. An elevated eosinophil count indicates an allergic condition or the presence of such parasites as heartworms or intestinal worms. This may indicate weaknesses in the thymus and adrenals. This may also indicate the requirement for vitamin B6 and vitamin C.

The blood test score for Platelet Count is 389, which is normal but above optimal. An elevated platelet count may indicate thickening of the blood or an inflammation of the bone marrow. This may also indicate a weakness in the bone marrow, as well as deficiencies of vitamin C and vitamin E.

Once the blood test scores are obtained and it is determined whether they fall within the optimal range, within the normal range but outside of optimal, or outside of the normal range, the specific nutraceuticals required to bring the animal to optimal health can be determined. As discussed above, different nutraceuticals may be required for each blood parameter that falls outside of the optimal range. The required nutraceuticals may also vary depending on whether the score falls above or below the optimal range.

For purposes of the example which follows, only the blood parameter albumin is considered. As indicated in Table 1 above, the blood test score for Albumin is 2, which is below the optimal range but within the normal range. As indicated above, low albumin levels indicate insufficient or poor quality protein in the diet. It may also indicate a degenerative disease and wasting or a sluggish metabolism of the liver. This often indicates the requirement for liver supplements, certain B vitamins, Vitamins A, C, and D, amino acids, and lecithin. For purposes of the following example, the calculation of the required dosage of a liver supplement for low albumin levels will be determined. It should be appreciated that the same formulas and methods apply to the determination of the other nutraceuticals indicated by the low albumin level (i.e., vitamins A, C, and D, and lecithin), as well as to the nutraceuticals indicated by the other blood test scores that fall outside the optimal ranges corresponding thereto.

In accordance with the present invention, if the blood chemical readings are determined to be outside of optimum range (step 2), they are grouped into Severity Ranges (e.g., −1, −2, −3 and +1, +2, +3) based on how far they deviate from optimum. Severity ranges may differ for each type of animal (canine, feline, equine, etc.). Each nutraceutical prescribed has a set of dosage properties, an example of which is shown in Table 2 below.

TABLE 2

CANINE DOSAGE CHART (Sample)

| Type of Ingredient | Weight of Ingredient | Frequency | (10) Strength (Low Dosage) | (25) Hi Cap | (26) Low Cap |
|---|---|---|---|---|---|
| Enzymes/Digestive Aids | | | | | |
| Bromelain | Dry | mg/lb | w/food | 1 | 200 | 20 |
| Betaine HCL | Dry | mg/lb | w/food | 1 | 200 | 20 |
| Pancreatin | Dry | u/lb | w/food | 250 | 40,000 | 4,000 |
| Pepsin | Dry | mg/lb | w/food | 0.6 | 200 | 15 |
| Glands | | | | | |

TABLE 2-continued

CANINE DOSAGE CHART (Sample)

| | Type of Ingredient | Weight of Ingredient | Frequency | (10) Strength (Low Dosage) | (25) Hi Cap | (26) Low Cap |
|---|---|---|---|---|---|---|
| Adrenal | Dry | mg/lb | BID | 2.65 | 500 | 35 |
| Bone Marrow | Dry | mg/lb | BID | 1.8 | 250 | 20 |
| Brain | Dry | mg/lb | BID | 1.5 | 500 | 50 |
| Heart | Dry | mg/lb | BID | 2 | 500 | 50 |
| Hypothalamus | Dry | mg/lb | BID | 0.35 | 35 | 5 |
| Intestines | Dry | mg/lb | BID | 2.1 | 600 | 35 |
| Kidney Gland | Dry | mg/lb | BID | 2.65 | 500 | 25 |
| Liver | Dry | mg/lb | BID | 4.5 | 600 | 60 |
| Lung | Dry | mg/lb | BID | 2.5 | 300 | 30 |
| Lymph | Dry | mg/lb | BID | 1.5 | 300 | 30 |
| Ovary/Uterus (Female Only) | Dry | mg/lb | BID | 2 | 300 | 25 |
| Pancreas | Dry | mg/lb | BID | 1.9 | 500 | 30 |
| Parathyroid | Dry | mg/lb | BID | 0.025 | 2.50 | 0.25 |
| Pineal | Dry | mg/lb | BID | 0.025 | 10 | 1 |
| Pituitary (Anterior) | Dry | mg/lb | BID | 0.75 | 125 | 15 |
| Pituitary (Whole) | Dry | mg/lb | BID | 0.75 | 125 | 15 |
| Prostate/Testes (Male Only) | Dry | mg/lb | BID | 2 | 300 | 25 |
| Salivary | Dry | mg/lb | BID | 0.8 | 125 | 35 |
| Spleen | Dry | mg/lb | BID | 2.25 | 500 | 35 |
| Stomach | Dry | mg/lb | BID | 2 | 500 | 30 |
| Thymus | Dry | mg/lb | BID | 2.65 | 600 | 35 |
| Thyroid | Dry | mg/lb | BID | 0.8 | 250 | 15 |

The set of dosage properties shown in Table 2 is used in conjunction with Table 3 below, which shows an example of a Nutritional Blood Test (NBT) Worksheet (NBTW) for a canine. Table 3 is an example of a primary chart for calculating the proper dosages.

TABLE 3

NUTRITIONAL BLOOD TEST (NBT) WORKSHEET - CANINE (Sample)
DOG WEIGHT: 75

| BLOOD CHEMICAL | (11) SEVERITY RANGE | (12) LOW RANGE VALUE | (13) HIGH RANGE VALUE | (14) NUTRA-CEUTICAL SUPPORT | (15) BLOOD CHEMICAL READING | (16) LOW DOSAGE MULTI-PLIER | (17) HIGH DOSAGE MULTI-PLIER (LOW DOSAGE × 2) | (18) MIN RANGE VALUE (−3) | (19) MAX RANGE VALUE (−1) |
|---|---|---|---|---|---|---|---|---|---|
| ALBUMIN | −3 | 1.6 | 1.9 | Liver | 2 | 4.5 | 9 | 1.6 | 2.6 |
| | | | | Vitamin A/D | | 35 | 70 | | |
| | | | | Vitamin C (Ascorbic) | | 6 | 12 | | |
| | | | | Vitamin C (Ester) | | 6 | 12 | | |
| | | | | Vitamin B Complex | | 1 | 2 | | |
| | | | | Lecithin Innositol Choline | | 7.5 | 15 | | |
| | −2 | 2 | 2.3 | Liver | | 4.5 | 9 | | |
| | | | | Vitamin A/D | | 35 | 70 | | |
| | | | | Vitamin C (Ascorbic) | | 6 | 12 | | |
| | | | | Vitamin C (Ester) | | 6 | 12 | | |
| | | | | Vitamin B Complex | | 1 | 2 | | |
| | | | | Lecithin Innositol Choline | | 7.5 | 15 | | |
| | −1 | 2.4 | 2.6 | Liver | | 4.5 | 9 | | |
| | | | | Vitamin A/D | | 35 | 70 | | |

TABLE 3-continued

NUTRITIONAL BLOOD TEST (NBT) WORKSHEET - CANINE (Sample)
DOG WEIGHT: 75

|   |   |   |   |   |   |
|---|---|---|---|---|---|
|   |   |   | Vitamin C (Ascorbic) | 6 | 12 |
|   |   |   | Vitamin C (Ester) | 6 | 12 |
|   |   |   | Vitamin B Complex | 1 | 2 |
|   |   |   | Lecithin Innositol Choline | 7.5 | 15 |
| 0 | 2.7 | 3.6 | OPTIMUM RANGE |  | 0 |
| 1 | 3.7 | 4.2 | Salivary | 0.8 | 1.6 |
|   |   |   | Lecithin Innositol Choline | 7.5 | 15 |
| 2 | 4.3 | 4.5 | Salivary | 0.8 | 1.6 |
|   |   |   | Lecithin Innositol Choline | 7.5 | 15 |
| 3 | 4.6 | 6 | Salivary | 0.8 | 1.6 |
|   |   |   | Lecithin Innositol Choline | 7.5 | 15 |

| BLOOD CHEMICAL | (14) Revised Support | (20) MIN RANGE VALUE (+1) | (21) MAX RANGE VALUE (+3) | (22) SLOPE (HIGH DOSE − LOW DOSE)/ (MAX RANGE − MIN RANGE) | (23) STRENGTH SLOPE × (CHEM READING − MAX RANGE) + HIGH DOSE | (24) DOSAGE AMOUNT STRENGTH × WEIGHT | (27) DOSAGE AMOUNT STRENGTH × WEIGHT (HI/LOW CAP APPLIED) |
|---|---|---|---|---|---|---|---|
| ALBUMIN | Liver | 3.7 | 6 | 4.5 | 6.3 | 472.5 | 472.5 |
|  | Vitamin A/D |  |  | 35 | 49 | 3675 | 3675 |
|  | Vitamin C (Ascorbic) |  |  | 6 | 8.4 | 630 | 630 |
|  | Vitamin C (Ester) |  |  | 6 | 8.4 | 630 | 630 |
|  | Vitamin B Complex |  |  | 1 | 1.4 | 105 | 105 |
|  | Lecithin Innositol Choline |  |  | 7.5 | 10.5 | 787.5 | 787.5 |
|  | Liver |  |  | 4.5 | 6.3 | 472.5 | 472.5 |
|  | Vitamin A/D |  |  | 35 | 49 | 3675 | 3675 |
|  | Vitamin C (Ascorbic) |  |  | 6 | 8.4 | 630 | 630 |
|  | Vitamin C (Ester) |  |  | 6 | 8.4 | 630 | 630 |
|  | Vitamin B Complex |  |  | 1 | 1.4 | 105 | 105 |
|  | Lecithin Innositol Choline |  |  | 7.5 | 10.5 | 787.5 | 787.5 |
|  | Liver |  |  | 4.5 | 6.3 | 472.5 | 472.5 |
|  | Vitamin A/D |  |  | 35 | 49 | 3675 | 3675 |
|  | Vitamin C (Ascorbic) |  |  | 6 | 8.4 | 630 | 630 |
|  | Vitamin C (Ester) |  |  | 6 | 8.4 | 630 | 630 |
|  | Vitamin B Complex |  |  | 1 | 1.4 | 105 | 105 |
|  | Lecithin Innositol Choline |  |  | 7.5 | 10.5 | 787.5 | 787.5 |
|  | OPTIMUM RANGE |  |  | 0 | 0 | 0 |  |
|  | Salivary |  |  | 0.8 | 1.12 | 84 | 84 |
|  | Lecithin Innositol Choline |  |  | 7.5 | 10.5 | 787.5 | 787.5 |
|  | Salivary |  |  | 0.8 | 1.12 | 84 | 84 |
|  | Lecithin Innositol Choline |  |  | 7.5 | 10.5 | 787.5 | 787.5 |
|  | Salivary |  |  | 0.8 | 1.12 | 84 | 84 |

TABLE 3-continued

NUTRITIONAL BLOOD TEST (NBT) WORKSHEET - CANINE (Sample)
DOG WEIGHT: 75

| | | | | |
|---|---|---|---|---|
| Lecithin Innositol Choline | 7.5 | 10.5 | 787.5 | 787.5 |

Table 4 below provides a description of the terms used in Tables 2 and 3 above. The numbers which precede each term in Table 4 below represent the numbered columns where the terms are used in Tables 2 and 3 above.

TABLE 4

Summary of Nutritional Blood Test
Worksheet Terms and Descriptions

(11) Severity: A general indicator of how far a chemical test deviates from normal. Severity levels range from −3 to +3 and each level consists of a range of chemical readings.
(12) Low Range Value: The minimum point of each Severity level.
(13) High Range Value: The maximum point of each Severity level.
(14) Nutraceutical Support: The nutraceuticals prescribed.
(15) Blood Chemical Reading: The blood test score from Blood Testing Laboratory.
(16) Low Dosage Multiplier: The minimum nutraceutical strength prescribed for an animal regardless of weight or severity of blood analysis.
(17) High Dosage Multiplier: The maximum nutraceutical strength prescribed for an animal regardless of weight or severity of blood analysis. High Dosage is usually twice the Low Dosage amount.
(18) Min Range Value (−3): The lowest chemical reading at the −3 Severity Level.
(19) Max Range Value (−1): The highest chemical reading at the −1 Severity Level.
(20) Min Range Value (+1): The lowest chemical reading at the +1 Severity Level.
(21) Max Range Value (+3): The highest chemical reading at the +3 Severity Level.
(22) Slope: A multiplier used to calculate the strength of the dosage prescribed. Slope is derived from the following formula:
(High Dosage − Low Dosage)/(Max Range − Min Range).
(23) Strength: A number multiplied times the weight of an animal to determine the prescribed dosage. Strength is derived from the following formula: (Slope × (Chemical Reading − Max Range)) + High Dose).
(24) Pre-Cap Dosage: The amount derived from multiplying the Strength times the weight of the animal.
(25). Low Cap: The minimum Dosage Amount prescribed for an animal regardless of weight or severity of blood analysis.
(26) High Cap: The maximum Dosage Amount prescribed for an animal regardless of weight or severity of blood analysis.

The first step in determining the proper dosage for a neutraceutical is to determine if the blood chemical reading 15 in Table 3 above is above or below the optimum range. If the blood chemical reading is below optimum (−1, −2, or −3 severity range), then the Minimum Range Value 18 is the lowest reading in the −3 Severity Level and the Maximum Range Value 19 is the highest reading in the −1 Severity Level. If the blood score is above optimum range (+1, +2, or +3 severity range), then the Minimum Range Value 20 is the lowest reading in the +1 Severity Level and the Maximum Range Value 21 is the highest reading in the +3 Severity Level. Continuing the canine example as discussed above, a blood chemical reading of 2 for the blood parameter albumin was obtained, as shown in column 15 of Table 3 above. A blood chemical reading of 2 falls within the −2 severity range (having a low range value of 2 shown in column 12 and a high range value of 2.3 shown in column 13) for albumin at column 11. In the Table 3 example shown, the optimum range (indicated in column 14) for albumin is between 2.7 (the low range value shown in column 12) and 3.6 (the high range value shown in column 13). A blood chemical reading below the optimum Severity Range results in a minimum range of 1.6 and a maximum ranges of 2.6 and as shown in 18 and 19 of Table 3 respectively.

Table 2 is a sample of a Canine Dosage Chart. It should be appreciated that Table 2 shows only a portion of the Canine Dosage Chart which includes enzymes/digestive aids and glandulars. A complete Dosage Chart may also provide dosage information for a variety of vitamins, minerals, homeopathics, herbal supplements, and the like. Separate dosage charts may be provided for each type of animal. Using the appropriate Dosage Chart (e.g., Table 3 for a canine), the corresponding neutraceuticals in the appropriate severity range are located and the Low Dosage 10 (Table 2) is multiplied times 2 to get the High Dosage Multiplier as shown in 17 (Table 3). This results in all the parts necessary to calculate the Slope 22 (as shown at step 4 of FIG. 2). Slope is a term used to indicate the slope of a line created by the relationship between the highest and lowest severity points and the highest and lowest dosages. Slope is calculated by subtracting the Low Dosage from the High Dosage and dividing that number by the Minimum Range Value subtracted from the Maximum Range Value. The resulting equation reads:

Slope=(High Dosage−Low Dosage/Max Range Value−Min Range Value).

Continuing the canine example discussed above and using a liver supplement as an identified nutraceutical for a low albumin level (as discussed above in connection with Table 1), the Canine Dosage Chart (Table 2) indicates a low dosage (at column 10) for a liver supplement of 4.5. As the maximum dosage is the low dosage times 2, the maximum dosage for the liver supplement is 9. The multipliers for low and high dosages are shown in columns 16 and 17 of Table 3. Accordingly, for the canine example under consideration, the high dosage multiplier is 9, the low dosage multiplier is 4.5, the maximum range is 2.6 and the minimum range is 1.6. Therefore, the slope may be calculated as: Slope=(9−4.5)/(2.6−1.6)=4.5, as indicated in column 14 of Table 3.

Using Slope, it can be determined where the actual blood chemical reading falls in relationship to the Low Dosage and the High Dosage by subtracting the Maximum Range Value from the Blood Chemical Reading and multiplying that number times the Slope. The result is then added to the High Dosage to get the Strength 23 (as shown in step 5 of FIG. 2). The resulting equation reads:

Strength=Slope×(Blood Chemical Reading−Max Range Value)+High Dosage Multiplier.

For the above-referenced canine example, the strength may be calculated as: Strength=4.5(2−2.6)+9=6.3.

To determine the Pre-Cap Dosage Amount 24 (as shown in step 6 of FIG. 2), multiply Strength times the Weight of the animal. The Pre-Cap Dosage is defined as the dosage before the High Cap or Low Cap is applied. The resulting equation reads:

Pre-Cap Dosage Amount=Strength×Animal Weight.

The canine example shown in FIG. 2 indicates that the weight of the canine is 75 lbs. Therefore, the Pre-Cap Dosage Amount for this canine may be calculated as:

Pre-Cap Dosage Amount=6.3×75=472.5.

The Pre-Cap Dosage Amount is then compared to the Low Cap 26 and High Cap 25 shown in Table 2. If the amount is lower than the Low Cap then the actual Dosage Amount is equal to the Low Cap (step 7). If the amount is greater than the High Cap (step 8) then the actual Dosage Amount is equal to the High Cap. If the amount is between the High Cap 25 and the Low Cap 26, the actual dosage amount is equal to the Pre-Cap Dosage Amount.

As shown in columns 25 and 26 of Table 2 for the canine example, the High Cap for the liver supplement is 600 and the Low Cap is 60. The Pre-Cap dosage for the canine computed above is 472.5, which falls between the indicated High and Low Cap values shown on Table 2. Therefore, the Pre-Cap Dosage Amount will be the actual dosage amount in this canine example.

The process discussed above and shown in FIG. 2 is repeated for each blood parameter that falls outside of the optimal range established for that parameter, and for each nutraceutical identified for each of these blood parameters that are outside of the normal range (step 9 of FIG. 2). Table 5 below shows an example of calculated dosages for the required nutraceuticals determined by the present invention in response to the blood test results listed in Table 1 above.

TABLE 5

Calculated dosages of prescribed nutraceuticals

| | Dosage |
|---|---|
| Glandular Supplements | |
| Bone Marrow | 175 mg |
| Ovary/Uterus | 250 mg |
| Adrenal | 150 mg |
| Kidney | 200 mg |
| Liver | 472.5 mg |
| Pituitary Whole | 125 mg |
| Medicinal Supplements | |
| SOD | 100 mg |
| Mineral Supplements | |
| Trace Minerals | 50 mg |
| Nutrients | |
| I-acid microbials | 0.05 units |
| I-carintine | 50 mg |
| Lecithin Inositol Choline | 250 mg |
| Taurine | 85 mg |
| Vitamin Supplements | |
| Vitamin A/D | 1250 iu |
| Vitamin B Acid | 85 mg |
| Vitamin B6 | 80 mg |
| Vitamin C Complex | 550 mg |
| Vitamin E | 225 iu |
| LIQUID REMEDIES | |
| Female Drops | 13 drops BID-OA |
| Female Formula | 17 drops BID |
| Incontinence Drops | 13 drops BID-OA |
| Kidney/Bladder Formula | 17 drops BID-OA |
| Kidney/Ovarian/Adrenal Drops | 13 drops BID-OA |
| Pituitary Drops | 13 drops BID-OA |

The liquid remedies are custom blended formulas designed to address specific problems. Female Drops provide specific cellular, tissue and metabolic support for the ovaries, uterus and imbalances related to the female hormonal system (especially in spayed females). Female Formula is designed to help balance female hormones, and tone strengthen the productive system. Relieves ovarian and uterine pain and inflammation. In spayed females, it will help balance the other glands that are involved in female hormone production. Incontinence Drops provide homeopathic support for the urinary bladder and sphincter to improve control for urinary leakage. Kidney/Bladder Formula reduces inflammation and strengthens the entire urinary tract in conditions such as lower urinary tract disease (LUTD), nephritis, cystitis, urolithiasis and urethritis. Kidney/Ovarian/Adrenal Drops provide specific cellular and glandular support for the kidney, ovary and adrenal glands. Pituitary Drops provide tissue and glandular support for the pituitary gland.

It should now be appreciated that the present invention provides advantageous methods and systems for providing a nutraceutical program specific to an individual animal, which determines appropriate dosages of nutraceuticals for optimization of the animal's health.

Although the invention has been described in connection with various illustrated embodiments, numerous modifications and adaptations may be made thereto without departing from the spirit and scope of the invention as set forth in the claims.

What is claimed is:

1. A method of providing a nutraceutical program specific to an individual animal, comprising:
    drawing blood from the animal;
    analyzing the blood at a lab to obtain blood test results;
    scoring the blood test results to obtain at least one blood test score for at least one corresponding blood parameter;
    determining if the at least one blood test score falls outside a normal range defined for the corresponding blood parameter; and
    if said at least one blood test score falls within said normal range but outside of an optimal range within said normal range:
        identifying one or more nutraceuticals needed to bring the animal within the optimal range for the at least one corresponding blood parameter; and
        calculating a prescribed dosage amount for at least one of said one or more identified nutraceuticals for the animal based on at least said blood test score for said corresponding blood parameter and a deviation of the blood test score from the optimal range;
    if said at least one blood test score falls outside of said normal range:
        prescribing standard nutrients or medications in order to bring the at least one blood test score within said normal range.

2. A method in accordance with claim 1, wherein said animal comprises a human.

3. A method in accordance with claim 1, wherein said animal comprises one of a fish, an amphibian, a reptile, a bird, or a mammal.

4. A method in accordance with claim 1, wherein said animal belongs to one of the following groups of animals: livestock, cattle, pets, domesticated animals, zoo animals, or exotic animals.

5. A method in accordance with claim 1, wherein said identifying of said one or more nutraceuticals is based on at least one of animal type, animal physiology, animal biochemistry, data describing an observed physical condition of the animal, and data describing a medical diagnosis of the animal.

6. A method in accordance with claim 1, wherein the calculating of the prescribed dosage amount for a particular identified nutraceutical comprises:
calculating a pre-cap dosage amount based on said blood test score, said deviation of the at least one blood test score from the optimal range, animal type, animal weight, dosage strength information, and dosage limit information; and
comparing said calculated pre-cap dosage amount to a low-cap dosage amount and a high-cap dosage amount for the animal;
wherein:
if the pre-cap dosage amount is between the low-cap and high-cap dosage amounts, the prescribed dosage amount is equal to the pre-cap dosage amount;
if the pre-cap dosage amount is greater than the high-cap dosage amount, the prescribed dosage amount is equal to the hi-cap dosage amount; and
if the pre-cap dosage amount is less than the low-cap dosage amount, the prescribed dosage amount is equal to the low-cap dosage amount.

7. A method in accordance with claim 6, wherein:
the low-cap dosage amount is the minimal amount of an identified nutraceutical prescribed for an animal regardless of the animal weight or the deviation of the at least one blood test score from the optimal range; and
the high-cap dosage amount is the maximum amount of an identified nutraceutical prescribed for an animal regardless of the animal weight or the deviation of the at least one blood test score from the optimal range.

8. A method in accordance with claim 6, wherein said pre-cap dosage amount is equal to a dosage strength S times the weight of the animal.

9. A method in accordance with claim 8, wherein said dosage strength S is defined as:

$$S = \text{slope}(\text{blood test score} - \text{maximum range value}) + \text{High dosage}.$$

10. A method in accordance with claim 9, further comprising:
establishing a plurality of severity levels indicating a range of blood test scores which deviate from said optimal range;
wherein a negative severity level indicates a range of blood test scores below a minimum of said optimal range, and a positive severity level indicates a range of blood test scores above a maximum of said optimal range.

11. A method in accordance with claim 10, wherein:
if the at least one blood test score falls within a negative severity level:
the maximum range value is the highest value of the negative severity level closest to said optimal range; and
a minimum range value is the lowest value of the negative severity level furthest from said optimal range; and
if the at least one blood test score falls within a positive severity level:
the maximum range value is the highest value in the positive severity level furthest from said optimal range; and
the minimum range value is the lowest value in the positive severity level closest to said optimal range.

12. A method in accordance with claim 11, wherein slope is defined as:

$$\text{slope} = (\text{high dosage} - \text{low dosage})/(\text{said maximum range value} - \text{said minimum range value}).$$

13. A method in accordance with claim 12, wherein:
said low dosage indicates a minimum nutraceutical strength prescribed for an animal regardless of the animal weight or the severity level of said at least one blood test score; and
said high dosage is approximately double said low dosage.

14. A method in accordance with claim 1, wherein at least one of said normal range and said optimal range is derived from a database containing historical blood test scores for a plurality of animals.

15. A method in accordance with claim 14, wherein said database is updated with information regarding animal type, animal weight and blood test scores obtained from testing of various animals.

16. A method in accordance with claim 1, wherein said blood parameters comprise at least one of white blood cell information, red blood cell information, and blood chemistry information.

17. A method in accordance with claim 1, wherein said blood parameters correspond to the function of one or more organs of the animal.

18. A method in accordance with claim 1, wherein the nutraceuticals comprise at least one of vitamins, minerals, enzymes, amino acids, homeopathic supplements, herbal supplements, and raw glandular supplements.

19. A method in accordance with claim 1, wherein:
the blood test results are electronically communicated from the lab to a service provider;
the service provider scores the blood test results to obtain the at least one blood test score and calculates the prescribed dosage amounts;
the prescribed dosage amounts are electronically communicated from the service provider to a compound pharmacist; and
the compound pharmacist prepares a prescription containing the one or more identified nutraceuticals in accordance with the prescribed dosage amounts and ships the prescription to an owner or veterinarian for administration to the animal.

* * * * *